United States Patent [19]

Yabuta et al.

[11] 4,035,188

[45] July 12, 1977

[54] N-ALKOXYETHOXYETHYL-PHENYLENEDIAMINE COLOR DEVELOPING AGENTS

[75] Inventors: Kenji Yabuta; Kiyoshi Yamashita; Kiyoshi Futaki, all of Nagaokakyo, Japan

[73] Assignee: Mitsubishi Paper Mills, Ltd., Tokyo, Japan

[21] Appl. No.: 563,458

[22] Filed: Mar. 31, 1975

[30] Foreign Application Priority Data

Apr. 3, 1974 Japan ............................ 49-37600

[51] Int. Cl.[2] ................ G03C 5/30; C07C 107/06; C07C 93/14

[52] U.S. Cl. ........................... 96/66 R; 260/207.5; 260/573

[58] Field of Search ..................... 260/573, 501.19; 96/66 R

[56] References Cited

U.S. PATENT DOCUMENTS

| | | | |
|---|---|---|---|
| 2,684,893 | 7/1954 | Hughes et al. ................ | 260/573 X |
| 3,656,950 | 3/1972 | Bent et al. .................... | 260/577 X |

*Primary Examiner*—Daniel E. Wyman
*Assistant Examiner*—John J. Doll
*Attorney, Agent, or Firm*—Cushman, Darby & Cushman

[57] ABSTRACT

Novel compounds represented by the following general formula are useful as color developing agents for color development which react with couplers to form color images:

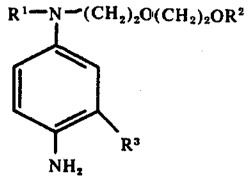

(wherein $R^1$ and $R^2$ which may be the same or different represent alkyl groups of 1 to 4 carbon atoms and $R^3$ represents hydrogen atom or methyl group).

10 Claims, No Drawings

N-ALKOXYETHOXYETHYLPHENYLENEDIAMINE COLOR DEVELOPING AGENTS

BACKGROUND OF THE INVENTION

The present invention relates to a novel developing agent for color photography and more particularly it relates to an improvement in p-phenylenediamine type developing agents which are used with couplers to form color images.

The color developing solution used for color development after color photographic material is exposed contains (1) a color developing agent which reduces silver halide and simultaneously is oxidized to cause coupling reaction with coupler to form color, (2) a preservative such as sodium sulfite, hydroxylamine, etc. which prevents the developing agent from being deteriorated due to oxidation with air, (3) a buffer which stabilizes the developing solution at a high pH to obtain a high developing activity, (4) an anti-fogging agent, and (5) benzyl alcohol for acceleration of the coupling reaction. Moreover, the developing solution may contain polyethylene glycols, surfactants, auxiliary developers. etc.

In the color development, the exposed silver halide is reduced to silver by development and on the other hand the developing agent is oxidized to form an oxidation product of the color developing agent, which effects coupling reaction with coupler under alkaline conditions to form a color image. It is known to use p-phenylenediamine derivatives as color developing agent for obtaining a color image using the oxidizing ability of said exposed silver halide.

However, not all of silver halide particles having a latent image are developed into silver and in order to obtain an image of high quality it has been demanded to provide a color developing process which can increase the ratio of the produced dye to the exposed silver halide than the conventional developing agent. Furthermore, recently it has been demanded to provide photographic developing solution from which benzyl alcohol which has been used for acceleration of development is omitted to prevent environmental pollution. However, development with the conventional developing agent without benzyl alcohol resulted in extreme reduction in density. By use of the color developing agent of the present invention, color images which have sufficiently excellent density and show substantially no change in hue can be obtained regardless of the presence of benzyl alcohol.

Moreover, the procedure for preparing color developing solutions by weighing various components of the developing solutions in correct proportions and dissolving them requires long time and great power of man. Therefore, developing solutions previously prepared in correct proportions have been demanded. A method by which color developing solutions can be obtained only by mixing several kinds of components and diluting them is very advantageous. However, from the point of transportation, a high concentration of the developing solution is required and so it is required that the color developing solution has a high solubility.

It is also desired that the color images formed by the coupling reaction are stable for a long period of time under exposure to heat, light and high humidity.

SUMMARY OF THE INVENTION

It is, therefore, an object of the present invention to provide a novel color developing solution which provides a greater ratio of produced dye to exposed silver halide than the conventional developing agents and can more effectively utilize the exposed silver halide, namely, has higher color developing efficiency.

It is another object of the present invention to provide a novel color developing agent which can form sufficiently excellent color images even when it is used in a developing solution containing no benzyl alcohol.

It is a further object of the present invention to provide a novel color developing agent which exhibits higher solubility than the conventional developing agents.

Also, it is yet another object of the present invention to provide a novel color developing agent capable of producing color images stable for a long period of time under exposure to heat, light and moisture.

DESCRIPTION OF THE PREFERRED EMBODIMENTS

The color developing agents of the present invention include those of the following general formula:

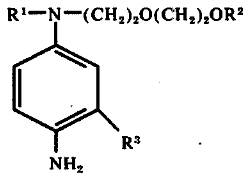

(wherein $R^1$ and $R^2$ which may be the same or different and represent alkyl groups of 1 – 4 carbon atoms such as methyl, ethyl, propyl, and butyl, and $R^3$ is a hydrogen atom or methyl group.).

Typical examples of these color developing agents represented by the above general formula are shown below, but the present invention should not be limited to these compounds.

Compound No. 1. N-ethyl-N-[β-(β-methoxy)ethoxy]ethyl-3-methyl-p-phenylenediamine Compound No. 2. N-ethyl-N-[β-(β-ethoxy)ethoxy]ethyl-3-methyl-p-phenylenediamine Compound No. 3. N-ethyl-N-[β-(β-butoxy)ethoxy]ethyl-3-methyl-p-phenylenediamine Compound No. 4. N-methyl-N-[β-(β-methoxy)ethoxy]ethyl-3-methyl-p-phenylenediamine Compound No. 5. N-methyl-N-[β-(β-ethoxy)ethoxy]ethyl-3-methyl-p-phenylenediamine Compound No. 6. N-ethyl-N-[β-(β-methoxy)ethoxy]ethyl-p-phenylenediamine Compound No. 7. N-ethyl-N-[β-(β-ethoxy)ethoxy]ethyl-p-phenyldiamine The fact that use of the color developing agents of the present invention can provide a greater ratio of produced dye to silver halide, in other words, can produce a color image by smaller amount of silver, than the conventional developing agent will be explanied in more detail.

The novel color developing agents claimed in the present application, e.g., N-ethyl-N-[β-(β-ethoxy)ethoxy]ethyl-3-methyl-p-phenylenediamine exhibit higher sensitivity, higher maximum density of color image and greater γ-value than the conventional color developing agents such as N-ethyl-N-(β-methanesulfonaminoethyl)-3-methyl-p-phenylenediamine (Compound No. 8) and N-ethyl-N-(β-hydroxyethyl)-3-methyl-p-phenylenediamine (Compound No. 9) when they are used in developing solution in which other components are same. This fact shows that the color developing agent of the present invention provides a greater ratio of produced dye to silver halide than the conventional developing agents do and moreover is much superior in photographic developing characteristics to the conventional developing agents.

Furthermore, in the system containing no benzyl alcohol, the conventional color developing agents such as said compounds Nos. 8 and 9 show sub-absorptions at 520 – 540 nm in color development of silver halide photosensitive material containing a yellow coupler to yield cloudy color and to cause reduction in purity of color image while no such tendency is seen in the color developing agent of the present invention.

It is one of the important characteristics of the novel color developing agent of the present invention that change in hue due to whether benzyl alcohol is added or not is small.

Moreover, regarding superiority in solubility of the developing agent, the developing agent represented by said general formula may be advantageously used as a free base or as a salt of inorganic acid or organic acid. For example, hydrochloride, sulfate, phosphate, oxalate, p-toluenesulfonate, benzenedisulfonate and aromatic sulfonate salts may be advantageously used. Among them, p-toluenesulfonate is especially excellent in solubility.

With reference to stability of color image against heat, light and moisture, the color developing agent of the present invention yields more stable color images than the conventional developing agents such as compound No. 8.

The compound of the present invention represented by said general formula is novel and method for preparation thereof will be explained below.

PREPARATION EXAMPLE 1

N-ETHYL-N-[β-(β-ETHOXY)ETHOXY]ETHYL-3-METHYL-P-PHENYLENEDIAMINE, DI-P-TOLUENESULFONATE

I. [β-(β-ethoxy)ethoxy]ethyl bromide 215 g (1.6 mole) of diethylene glycol monoethyl ether was introduced into a 1 *l* three-necked flask and slightly warmed by a mantle heater. Then, 135.4 g (0.5 mole) of phosphorus tribromide was slowly added dropwise over a period of 2 hours. The reaction mixture was cooled and poured into 500 cc of water. The desired oily product accumulated at the bottom was extracted with ether and the extract was washed with 100 cc of 10% sulfuric acid two times and with 10% sodium carbonate two times. After further washing with water two times, the extract was dried with potassium carbonate to remove ether, followed by distillation of the residue oil under reduced pressure. After removing the inital fraction of low boiling point, fractions having boiling point of 96° – 98° C/30 mmHg were collected. The yield of (I) was about 40%.

II. N-ethyl-N-[β-ethoxy[β-ethoxy)]ethyl-3-methylaniline

A mixture of 67.5 g(0.5 mole) of N-ethyl-3-methylaniline, 98.5 g (0.5 mole) of [β-(β-ethoxy)-ethoxy]ethyl bromide, 44.1 g (0.55 mole) of sodium bicarbonate, 5.50 ml of ethanol and 145 ml of water was refluxed for 80 hours. Ethanol was removed by distillation and the oil layer was extracted with ether. The extract was dried with potassium carbonate and then ether was removed, followed by distillation of the residue oil under reduced pressure.

Fractions having boiling point of 150° – 155° C/1 mmHg were collected. yield of (II) was about 70%.

III. 4-(2,5-dichlorophenylazo)-N-[β-(β-ethoxy-ethoxy]ethyl-N-ethyl-3-methylaniline 3.22 g(0.02 mole) of 2,5-dichloroaniline was dissolved in a mixed solution of 17 ml of concentrated hydrochloric acid and 50 ml of water while stirring with heat on a water bath and cooled to 5° C, to which a solution prepared by dissolving 2.7 g (0.025 mole) of sodium nitrite in 10.6 ml of water was slowly added dropwise. Temperature was kept at 5° C and after completion of the addition, this was stirred for 20 minutes and then sulfamic acid was added thereto to decompose excess $HNO_2$. Thereafter, the solution was filtered and added at a time to a solution prepared by dissolving 5.02 g (0.02 mole) of N-[β-(β-ethoxy) ethoxy]ethyl-N-ethyl-3-methylaniline in 200 cc of 1N-HCl. Then, about 300 ml of water was added thereto and 18.5 g of sodium acetate was added with stirring to make the solution weakly acidic. After being allowed to stand for several hours, the solution was filtered. The azo dye sticking to the wall of device and filter paper was collected and used for the next reaction without purification. The crude product was 8.2 g.

IV. N-ethyl-N-[β-(β-ethoxy)ethoxy]ethyl-3-methyl-p-phenylenediamine-di-p-toluenesulfonate 4.23 g (0.01 mole) of the azo dye prepared in (III) was reduced with 250 ml of ethyl alcohol using palladium-carbon as a catalyst on a Paal-shaker. After completion of the reaction, the catalyst was filtered out and further washed with a large amount of ethanol on a funnel. To the filtrate was added a solution prepared by dissolving 3.8 g (0.02 mole) of p-toluenesulfonic acid in 70 ml of ethyl alcohol and then the solution was concentrated to dryness.

Thereafter, to the semisolid was added about 20 ml of ethyl acetate to separate white microcrystals, which were filtered off. The solid was dissolved in about 20 ml of hot isopropyl alcohol. To the solution was slowly added 50 ml of ethyl acetate at room temperature to cause reprecipitation. The crystals separated were filtered off to obtain color developing agent in the form of a salt which had a melting point of 170°–173.5° C and yield was about 70%.

PREPARATION EXAMPLE 2

N-ethyl-N-[β-(β-methoxy)ethoxy]ethyl-3-methyl-p-phenylenediamine, di-p-toluenesulfonate In the same manner as in Preparation Example 1, the above compounds may be produced using N-ethyl-3-methylaniline and diethylene glycol monomethyl ether.

I. [β-(β-methoxy)ethoxy]ethyl bromide 192 g (1.6 mole) of diethylene glycol monomethyl ether was introduced into a 1 *l* three necked flask and slightly warmed by a mantle heater. Thereto was slowly added dropwise 135.4 g (0.5 mole) of phosphorus tribromide over a period of 2 hours. The reaction mixture was cooled and poured to 500 cc of water. The desired oily product accumulated at the bottom was extracted with ether and the extract was washed with 10% sulfuric acid, 10% sodium carbonate and water and was dried. After removal of ether, fractions having boiling point of 99°–100° C/30 mmHg were collected. The yield of (I) was about 20%.

II. N-[β-(β-methoxy)ethoxy]ethyl-N-ethyl-3-methylaniline

A mixture of 33.7 g (0.25 mole) of N-ethyl-3-methylaniline, 45.5 g (0.25 mole) of [β-(βmethoxy) ethoxy]ethylbromide, 25.2 g (0.3 mole) of sodium bicarbonate, 275 ml of ethanol and 72.5 ml of water was refluxed for 100 hours. Ethyl alcohol was removed by distillation and the oil layer was extracted with ether. The extract was dried with potassium carbonate and ether was removed, followed by distillation of the residue oil under reduced pressure. Fractions having boiling point of 135° c – 137° C/1 mmHg were collected. Yield of (II) was about 70%.

III. 4-(2,5-dichlorophenylazo)-N-[β-(β-methoxy) ethoxy]ethyl-N-ethyl-3-methylaniline 8.1 g (0.05 mole) of 2,5-dichloroaniline was dissolved in a mixed solution of 40 ml of concentrated hydrochloric acid and 130 ml of water while stirring with heat on a water bath. The solution was cooled in 5° C and a solution prepared by dissolving 3.8 g (0.055 mole) of sodium nitrite in 23.5 ml of water was slowly added dropwise. The temperature was kept at 5° C and after completion of the addition, it was stirred for 20 minutes and then sulfamic acid was added to decompose excess $HNO_2$. Thereafter, the solution was filtered and added at a time to a solution obtained by dissolving 11.8 g (0.05 mole) of N-[β-(β-methoxy) ethoxy]ethyl-N-ethylaniline in 500 cc of 1N-HCl. 500 ml of water was added thereto and with stirring 46.25 g of sodium acetate was additionally added to make the liquid weakly acidic. This was allowed to stand for several hours and then filtered. The azo dye which adhered to wall of the device and filter paper was collected and used for the next reaction without purification.

IV. N-ethyl-N-[β-(β-methoxy)ethoxy]ethyl-3-methyl-p-phenylenediamine, di-p-toluenesulfonate 20.45 g (0.05 mole) of the azo dye prepared in (III) was reduced with use of 350 ml of ethyl alcohol and palladium-carbon as a catalyst on Paalshaker. After completion of the reaction, the catalyst was filtered out and washed with a large amount of ethanol. To the filtrate was added a solution obtained by dissolving 19 g (10.1 mole) of p-toluenesulfonic acid in 350 ml of ethyl alcohol and then the resultant solution was concentrated to dryness.

To thus obtained semisolid was added about 50 ml of ethyl acetate to separate with microcrystals, which were filtered off. This solid was dissolved in 30 ml of hot isopropyl alcohol and the solution was allowed to stand overnight and then filtered to obtain 27.0 g of the developing agent in the form of a salt. This salt had a melting point of 186°–188° C and the yield was about 90%.

PREPARATION EXAMPLE 3

N-ethyl-N-[β-(β-ethoxy)ethoxy]ethyl-p-phenylenediamine-di-p-toluenesulfonate

I. N-[β-(β-ethoxy)ethoxy]ethyl-N-ethyl-aniline

A mixture of 60.5 g (0.5 mole) of N-ethylaniline, 98.5 g (0.5 mole) of [β-(β-ethoxy)ethoxy]ethyl bromide, 44.1 g (0.55 mole) of sodium bicarbonate, 550 ml of ethyl alcohol and 145 ml of water was refluxed for 100 hours. Ethyl alcohol was removed by distillation and the oil layer was extracted with ether. Thereafter, the extract was dried with potassium carbonate and ether was removed, followed by distillation of the residue oil under reduced pressure. Fractions having boiling point of 162°–165° C/1 mmHg were collected. Yield of (I) was about 30%.

II. 4-(2,5-dichlorophenylazo)-N-[β-(β-ethoxy) ethoxy]ethyl-N-ethylaniline 16.1 g (0.1 mole) of 2,5-dichloroaniline was dissolved in a mixed solution of 85 ml of concentrated hydrochloric acid and 200 ml of water while stirring with heating on a water bath and the solution was cooled to 5° C and a solution prepared by dissolving 8.28 g (0.12 mole) of sodium nitrite in 50 ml of water was slowly added dropwise. The temperature was kept at 5° C and after completion of the addition of the solution was stirred for 20 minutes, sulfamic acid was added thereto to decompose excess $HNO_2$. Thereafter, the solution was filtered and added at a time to a solution prepared by dissolving 23.6 g (0.1 mole) of N-[β-(β-ethoxy)ethoxy]ethyl-N-ethylaniline in 1 *l* of 1N-HCl. Furthermore, about 500 ml of water was added thereto and with stirring about 200 g of sodium acetate were added thereto. After allowing to stand for several hours, it was filtered and the azo dye which adhered to wall of device and filter paper was collected and used for the next reaction without purification. The crude product was 34.1 g.

III. N-ethyl-N-[β-(β-ethoxy)ethoxy]ethyl-p-phenylenediamine, di-p-toluenesulfonate 20.4 g (0.05 mole) of the azo dye prepared in (II) was reduced with use of 300 ml of ethyl alcohol and palladium-carbon as a catalyst on Paal-shaker. After completion of the reaction, the catalyst was filtered off and washed with a large amount of ethanol on a funnel.

To the filtrate was added a solution prepared by dissolving 19 g (0.1 mole) of p-toluenesulfonic acid in 350 ml of ethyl alcohol and the resultant solution was concentrated to dryness. Next, to the semisolid was added a small amount of ethyl acetate to separate white microcrystals, which were filtered off. This solid was dissolved in 30 ml of hot isopropyl alcohol and the solution was allowed to stand overnight, followed by filtration to obtain 20 g of developer in the form of a salt, which had a melting point of 163.5°–166° C and the yield was about 70%.

The following examples illustrate the present invention.

EXAMPLE 1

A gelatin-silver iodobromide emulsion containing yellow coupler was prepared using α-pivalyl-2-chloro-5-[γ-(2,4-di -t-amylphenoxybutylamide)] acetanilide aws a coupler and di-n-butylphthalate as a solvent for the coupler. The resultant emulsion was coated on an under-coated polyester film. The coated light sensitive layer contained 10 parts by weight of gelatin, 5 parts by weight of silver halide, 3 parts by weight of coupler and 2 parts by weight of solvent for the coupler and amount of coupler in the coat was $3.3 \times 10^{-3}$ mole/$m^2$. Thus produced light sensitive material was exposed through a step tablet and then was developed for 6 minutes with a developing solution of the following compositions. In the developing solution, compounds No. 1 and 2 which are the present color developing agents and the following known color developing agents (Compounds Nos. 8′ and 9′) for comparison were used as the color developing agent.

Compound No. 8': N-ethyl-N-(β-methanesulfonamide-thyl)-3-methyl-p-phenylenediamine sesquisulfate monohydrate Compound No. 9': N-ethyl-N-(β-hydroxyethyl)-3-methyl-p-phenylenediamine monosulfate.

DEVELOPING SOLUTION 1

| | |
|---|---|
| Sodium hydroxide | 1.65 g |
| Sodium metaborate | 50 g |
| Anhydrous sodium sulfite | 1.8 g |
| Potassium bromide | 0.5 g |
| Color developing agent | 5.0 g |
| Sodium hexametaphosphate | 0.5 g |
| Hydroxylamine hydrochloride | 1.0 g |
| Benzyl alcohol | 12 ml |
| Diethylene glycol | 10 ml |
| Water to make 1 l | |

DEVELOPING SOLUTION 2

| | |
|---|---|
| Sodium hydroxide | 1.65 g |
| Sodium metaborate | 50 g |
| Anhydrous sodium sulfite | 1.8 g |
| Potassium bromide | 0.5 g |
| Color developing agent | 5.0 g |
| Sodium hexametaphosphate | 0.5 g |
| Hydroxylamine hydrochloride | 1.0 g |
| Diethylene glycol | 10 ml |
| Water to make 1 l | |

Then, the developed light sensitive materials were bleached and fixed for 4 minutes with EDTA-iron salt bleaching and fixing liquid of the following compositions.

| | |
|---|---|
| EDTA-iron salt | 56 g |
| EDTA-disodium salt | 2 g |
| Ammonium thiosulfate | 60 g |
| Anhydrous sodium sulfite | 20 g |
| Acid sodium sulfite | 5 g |
| Phosphoric acid-disodium salt | 12 g |
| Water to make 1 l | |

Then, they were washed with water for 8 minutes, dipped in a stabilizing bath for 3 minutes and then dried.

Thus, color images were obtained in the cases of the developing solutions containing benzyl alcohol and containing no benzyl alcohol.

Luminous reflectance, excitation purity and dominant wavelength of thus obtained yellow color images at each step tablet were calculated in accordance with JIS-Z8701. The results are shown in the following Table 1.

The numerical values in Table 1 indicate excitation purity (%) and dominant wavelength (nm) of the obtained yellow images having a luminous reflectance of 60%.

Table 1

| Color developing agent | Excitation purity (%) | | Dominant wavelength (nm) | |
|---|---|---|---|---|
| | Developing solution 1 | Developing solution 2 | Developing solution 1 | Developing solution 2 |
| Compound No. 1* | 76 | 57 | 578.1 | 577.6 |
| Compound No. 2* | 67 | 66 | 577.4 | 577.6 |
| Compound No. 8' | 72 | 30 | 578.1 | 581.9 |
| Compound No. 9' | 64 | 26 | 578.5 | 583.0 |

*Color developing agent of the present invention.

As is clear from Table 1, when Compounds No. 8' and No. 9' which were conventional color developing agents were used and the developing solution contained no benzyl alcohol, hue of the images became cloudy, dominant wavelength was changed and it is very difficult to reproduce a color exactly corresponding to the original color while the color developing agents of the present invention had no such defects and can also be advantageously used in the system containing no benzyl alcohol.

EXAMPLE 2

A blue sensitive emulsion containing yellow coupler, a green sensitive emulsion cntaining magenta coupler and a red sensitive emulsion containing cyan coupler were coated in this order together with intermediate layers which separated each layer of the emulsions on a paper support which had been previously coated with polyethylene film. Compound No. 10 as the yellow coupler, Compound No. 11 as the magenta coupler and Compound No. 12 as the cyan coupler were used.

Compound 10

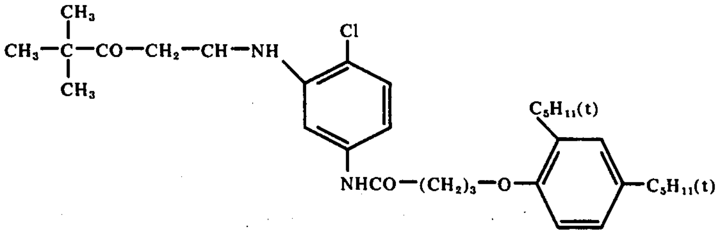

Compound 11

-continued

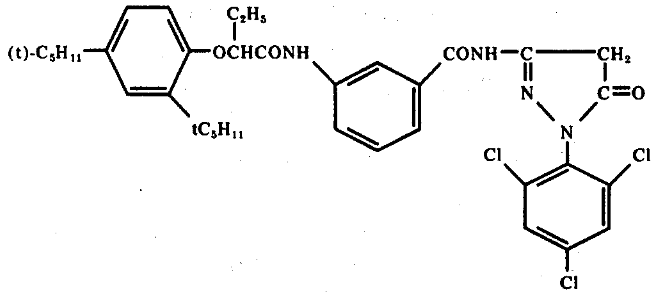

Compound 12

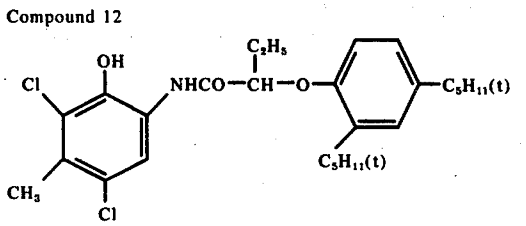

Compositions of each layer were 10 parts by weight of gelatin, 5 parts by weight of silver halide, 3 parts by weight of coupler and 2 parts by weight of solvent for the coupler and amount of coupler in the coat was 3.3 $\times 10^{-3}$ mole/$m^2$. Thus obtained light sensitive materials were exposed in three-color separation method through step tablet and then were subjected to developing-bleaching and fixing-stabilizing treatments in the same manner as in Example 1. Density of thus obtained color image was measured by a densitometer (RD-400 manufactured by Macbeth Co., Ltd.) to obtain maximum density and $\gamma$. The results are shown in Tables 2 and 3. As color developing agents for comparison, the conventional color developing agents used in Example 1 and the following conventional color developing agent Compound No. 13 were used.

Compound No. 13 : N-ethyl-N-($\beta$-ethoxyethyl)-3-methyl-p-phenylenediamine, di-p-toluene-sulfonate Table 2

| | Maximum-density | | | | | |
|---|---|---|---|---|---|---|
| | Yellow | | Magenta | | Cyan | |
| | Developing solution 1 | Developing solution 2 | Developing solution 1 | Developing solution 2 | Developing solution 1 | Developing solution 2 |
| Compound No. 2* | 2.13 | 1.78 | 2.20 | 2.25 | 2.24 | 2.30 |
| Compound No. 8' | 2.00 | 0.95 | 2.12 | 2.12 | 2.37 | 1.89 |
| Compound No. 9' | 2.15 | 1.25 | 2.09 | 2.10 | 2.24 | 2.03 |
| Compound No. 13 | 1.99 | 1.35 | 2.14 | 2.26 | 2.21 | 2.24 |

*Color developing agent of the present invention.

Table 3

| | $\gamma$-values | | | | | |
|---|---|---|---|---|---|---|
| | Yellow | | Magenta | | Cyan | |
| | Developing solution 1 | Developing solution 2 | Developing solution 1 | Developing solution 2 | Developing solution 1 | Developing solution 2 |
| Compound No. 2* | 2.08 | 1.49 | 2.50 | 2.13 | 2.38 | 2.50 |
| Compound No. 8' | 1.54 | — | 2.13 | 1.75 | 2.33 | 1.69 |
| Compound No. 9' | 1.78 | — | 2.33 | 1.69 | 2.56 | 2.12 |
| Compound No. 13 | 2.00 | 0.89 | 2.50 | 2.17 | 2.38 | 1.92 |

*The color developing agent of the present invention "—" means that $\gamma$ was less than 0.6.

As is clear from Tables 2 and 3, the color developing agent of the present invention provided color images higher in density and greater in $\gamma$ than those of the images obtained by the conventional color developing agents. This fact proves that the color developing agents of the present invention produce dye of color image (in connection with exposed silver halide) more advantageously than the conventional developing agents. Furthermore, the color developing agent of the present invention can provide color images which are of not greatly soft tone and have a high density even when the developing solution contains no benzyl alcohol. This fact proves that the color developing agents of the present invention are suitable as those demanded for prevention of environmental pollution.

EXAMPLE 3

In the same manner as in Example 2, blue sensitive emulsion, green sensitive emulsion, ultraviolet absorbing layer and red sensitive emulsion were coated in this order on a paper support which had been previously coated with a polyethylene film. Coating of the intermediate layers and couplers used were the same as in Example 2. As the ultraviolet absorbing agent, 2N-(2-hydroxy-3,5-di-tert-amylphenyl) benzotriazole was used and amount of this ultraviolet absorbing agent coated was 0.8 g/$m^2$.

Thus produced photographic light sensitive materials were exposed in three-color separation method through a step tablet and developed with developing solution 1 prepared in Example 1. Thereafter, these light sensitive materials were subjected to bleaching and fixing, washing with water and stabilizing treatments to obtain step tablet images. Density of thus obtained color images was measured by said densitometer and thereafter, the images were subjected to fade test consisting of exposing them to carbon arc lamp for 40 hours and measuring the fade by Standard Fade Meta FA-1 of Tokyo Rika K.K. The results are shown in Table 4. The numerical values indicate decrement of density of the color image which had the density of 1 before the test. Filters used in the densitometer were Ratten filter No. 47 for yellow image, Ratten filter No. 58 for magneta image, and Ratten filter No. 25 for cyan image. As the conventional color developing agents for comparison, said compounds No. 8', No. 9' and No. 13 were used.

Table 4

| | Yellow image | Magenta image | Cyan image |
|---|---|---|---|
| Compound No. 1* | 0.30 | 0.08 | 0.25 |
| Compound No. 8' | 0.32 | 0.13 | 0.29 |
| Compound No. 9' | 0.43 | 0.15 | 0.46 |
| Compound No. 13 | 0.45 | 0.14 | 0.28 |

*Color developer of the present invention

As is clear from Table 4, the image obtained using the color developing agent of the present invention was faster than the images obtained usng the conventional color developing agents.

What is claimed is:

1. In a color developing solution containing a color developing agent, a preservative, a buffer and an antifogging agent the improvement comprising employing as the color developing agent a compound of the formula

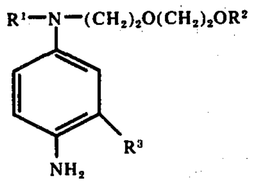

wherein $R^1$ and $R^2$ are alkyl of 1 to 4 carbon atoms and $R^3$ is hydrogen or methyl or a salt thereof.

2. A color developing solution according to claim 1 including benzyl alcohol for acceleration of the coupling reaction.

3. A color developing solution according to claim 1 wherein $R^3$ is methyl.

4. A color developing solution according to claim 1 wherein $R^1$ is ethyl and $R^3$ is methyl and said compound is a salt of an aromatic sulfonic acid.

5. A color developing solution according to claim 4 wherein the salt is a salt of p-toluene sulfonic acid.

6. A color developing solution according to claim 1 wherein the compound is N-ethyl-N-[β-(β-methoxy) ethoxy]ethyl-3-methyl-p-phenylenediamine or a salt thereof.

7. A color developing solution acording to claim 1 wherein the compound is N-ethyl-N-[β-(β-ethoxy) ethoxy]ethyl-3-methyl-p-phenylenediamine or a salt thereof.

8. A color developing solution according to claim 1 wherein the compound is N-ethyl-N-[β-(β-butoxy) ethoxy]ethyl-3-methyl-p-phenylenediamine or a salt thereof.

9. A color developing solution according to claim 1 wherein the compound is N-methyl-N-[β-(β-methoxy) ethoxy]ethyl-3-methyl-p-phenylenediamine or a salt thereof.

10. A color developing solution according to claim 1 wherein the compound is N-methyl-N-[β-(β-ethoxy) ethoxy]ethyl-3-methyl-p-phenylenediamine or a salt thereof.

* * * * *